US007179084B1

(12) United States Patent
Kometas

(10) Patent No.: US 7,179,084 B1
(45) Date of Patent: Feb. 20, 2007

(54) APPARATUS AND METHOD TO REMOVE DENTAL IMPLANT

(76) Inventor: Athas N. Kometas, 3162 S. Atlantic Ave., Daytona Beach Shores, FL (US) 32118

( * ) Notice: Subject to any disclaimer, the term of this patent is extended or adjusted under 35 U.S.C. 154(b) by 0 days.

(21) Appl. No.: 11/204,449

(22) Filed: Aug. 16, 2005

(51) Int. Cl.
*A61C 3/00* (2006.01)
(52) U.S. Cl. .................. 433/75; 433/173; 433/165; 606/99
(58) Field of Classification Search ............... 433/75, 433/173, 174, 176, 165; 606/99, 96, 80
See application file for complete search history.

(56) References Cited

U.S. PATENT DOCUMENTS

| 1,123,730 | A | 1/1915 | Greenfield | |
|---|---|---|---|---|
| 1,216,683 | A | 2/1917 | Greenfield | |
| 1,438,168 | A | 12/1922 | Brown | |
| 3,979,829 | A | 9/1976 | Lemos | |
| 4,820,156 | A | 4/1989 | Ross | |
| 5,085,586 | A | 2/1992 | Johnson | |
| 5,201,656 | A | * | 4/1993 | Sicurelli, Jr. ............... 433/166 |
| 5,782,636 | A | * | 7/1998 | Armstrong et al. ......... 433/165 |
| 5,868,572 | A | * | 2/1999 | Lazzara et al. ............ 433/173 |
| 5,944,525 | A | * | 8/1999 | Ura ............................ 433/173 |
| 5,951,286 | A | | 9/1999 | Rhodes |
| 6,280,197 | B1 | | 8/2001 | Benado |
| 7,021,935 | B2 | * | 4/2006 | Aeby et al. ................. 433/224 |

* cited by examiner

*Primary Examiner*—Ralph A. Lewis
(74) *Attorney, Agent, or Firm*—Paul S. Rooy P.A.

(57) ABSTRACT

A method and apparatus to remove dental implant. The apparatus comprises a guide ring rotatably attached to a base, means to rotatably attach the guide ring to the base, means to attach the apparatus to an implant, and apparatus to remove dental implant indexing means sized to mate with implant indexing means when the apparatus is attached to the implant. Where an abutment is mounted to the implant, means of attaching the base to the abutment is taught. The method includes the steps of attaching the apparatus to an implant or abutment, sliding a trephine burr bore over the guide ring, and using the guide ring to guide the trephine while drilling into bone in which the implant is implanted, without drilling into the implant or abutment.

26 Claims, 8 Drawing Sheets

APPARATUS AND METHOD TO REMOVE DENTAL IMPLANT

BACKGROUND OF THE INVENTION

1. Field of the Invention

This invention relates to dental implants, and in particular to an apparatus and method to remove a dental implant.

2. Background of the Invention

Implants in a patient's jaw bone are routinely used in the dentistry arts to anchor individual prosthetic teeth as well as bridges containing a number of prosthetic teeth. As may be observed in FIG. 1, a side cross-sectional view of implant 2, an appropriate aperture is made in bone 4, implant 2 inserted, and then over time bone 4 grows over implant 2, thus securely anchoring it in place.

Referring now also to FIG. 2, a top view of implant 2 in bone 4, implant 2 typically comprises implant indexing means 6, and an implant connector 8. After implant 2 is firmly anchored in bone 4, a prosthesis is attached to it. Implant indexing means 6 is sized to mate with a matching prosthesis indexing means, in order to prevent rotating of the prosthesis relative to implant 2 after the prosthesis is installed on implant 2. While in FIGS. 1 and 2 implant indexing means 6 was an external hex, 2 implant indexing means 6 may be any appropriate shape, including but not limited to any external polygonal or other shape, any internal polygon or other shape, etc.

In FIGS. 1 and 2, implant connector 8 is a threaded bore 8, which may be used to attach a prosthesis to implant 2 by means of a threaded fastener sized to mate with the threaded bore which is implant connector 8.

On occasion it becomes necessary to remove an implant 2 which was previously 7 installed in bone 4. A trephine burr, such as trephine burr 10 depicted in FIG. 3, is used to accomplish this task. The trephine burr drills around the outside edge of implant 2 to a depth substantially equal to the depth of implant 2 within bone 4. Trephine burr 10 is then withdrawn and implant 2 lifted out of bone 4.

One problem associated with current trephine drilling procedures connected with implant extraction is the difficulty of maintaining trephine burr 10 parallel with implant 2, to prevent drilling into implant 2 with trephine burr 10. The result would be small chips of implant 2 left within bone 4. As most implants 2 are made of metal, these left-behind chips severely reduce visibility when subsequent X-rays are taken of the area. Given the importance of X-rays in the dental sciences as a diagnostic and evaluation tool, this is a serious consequence, indeed. Thus, it would be desirable to provide a means to hold trephine burr 10 correctly aligned with implant 2 during the implant removal operation.

A relatively recent development in dental implant technology involves mounting an abutment to a dental implant, and then mounting a prosthesis to the abutment. This configuration is depicted in FIGS. 12 and 14. In FIG. 12 abutment 12 is ready to be installed on implant 2, which installation is accomplished by mating abutment implant connector 14 with implant connector 8 as indicated by arrows 20 and 22 in FIG. 12. While FIGS. 12–16 illustrate abutment implant connector 14 as a threaded stud and implant connector 8 as a threaded bore, either may be any appropriate connector—for instance, abutment implant connector 14 could be a threaded bore and implant connector 8 could be a threaded stud, or abutment implant connector 14 and implant connector 8 may be any other appropriate pair of mating connectors.

When an abutment 12 attached to an implant 2 is to be removed from bone 4 in which it resides, an important problem associated with current trephine drilling procedures connected with this extraction is the difficulty of maintaining trephine burr 10 parallel with abutment 12 and implant 2, to prevent drilling into abutment 12 and/or implant 2 with trephine burr 10. The result would be small chips of abutment 12 and/or implant 2 left within bone 4. Where abutment 12 and/or implants 2 are made of metal, these left-behind chips severely reduce visibility when subsequent X-rays are taken of the area. Given the importance of X-rays in the dental sciences as a diagnostic and evaluation tool, this is a serious consequence. Thus, it would be desirable to provide a means to hold trephine burr 10 correctly aligned with abutment 12 and implant 2 during the implant removal operation.

SUMMARY OF THE INVENTION

Accordingly, it is an object of the present invention to provide an apparatus and method to remove dental implant which maintains the trephine burr properly aligned with the dental implant so as to avoid drilling into the dental implant during the extraction process. Design features allowing this object to be accomplished include a guide ring sized to slidably fit within a trephine burr bore rotatably attached to a base, and means to attach the base to the implant. Advantages associated with the accomplishment of this object include increased efficiency and reduced drilling into the implant.

Where an abutment is present, it is another object of the present invention to provide an apparatus and method to remove dental implant which maintains the trephine burr properly aligned with an abutment and dental implant so as to avoid drilling into the abutment and/or dental implant during the extraction process. Design features allowing this object to be accomplished include a guide ring sized to slidably fit within a trephine burr bore rotatably attached to a base, and means to attach the base to the abutment. Advantages associated with the accomplishment of this object include increased efficiency and reduced drilling into the abutment and implant.

It is another object of the present invention to provide a method to remove dental implant which maintains the trephine burr properly aligned with the dental implant so as to avoid drilling into the dental implant during the extraction process. Method steps to accomplish this include the steps of attaching the apparatus to an implant, sliding a trephine burr bore over a guide ring, and using the guide ring to guide the trephine while drilling into bone in which the implant is implanted, without drilling into the implant or abutment. Advantages associated with the accomplishment of this object include increased efficiency and reduced drilling into the implant.

Where an abutment is present, it is another object of the present invention to provide a method to remove dental implant which maintains the trephine burr properly aligned with an abutment and dental implant so as to avoid drilling into the abutment and/or dental implant during the extraction process. Method steps to accomplish this include the steps of attaching the apparatus to the abutment, sliding a trephine burr bore over a guide ring, and using the guide ring to guide the trephine while drilling into bone in which the implant is implanted, without drilling into the implant or abutment. Advantages associated with the accomplishment of this object include increased efficiency and reduced drilling into the abutment and implant.

It is yet another object of this invention to provide an apparatus and method to remove dental implant whose guide ring does not rotate relative to a trephine burr. Design features allowing this object to be achieved include at least one key on a guide ring, and a keyway on a trephine burr bore corresponding to each key sized to slidably admit a key. Benefits associated with reaching this objective include reduced wear between the guide ring and the trephine burr, and hence increased reliability and reduced cost.

BRIEF DESCRIPTION OF THE DRAWINGS

The invention, together with the other objects, features, aspects and advantages thereof will be more clearly understood from the following in conjunction with the accompanying drawings.

Eight sheets of drawings are provided. Sheet one contains FIGS. 1 and 2. Sheet two contains FIG. 3. Sheet three contains FIG. 4. Sheet four contains FIGS. 5–7. Sheet five contains FIGS. 8 and 9. Sheet six contains FIGS. 10 and 11. Sheet seven contains FIGS. 12 and 13. Sheet eight contains FIGS. 14 and 15.

DETAILED DESCRIPTION OF THE PREFERRED EMBODIMENT

Figure 1:
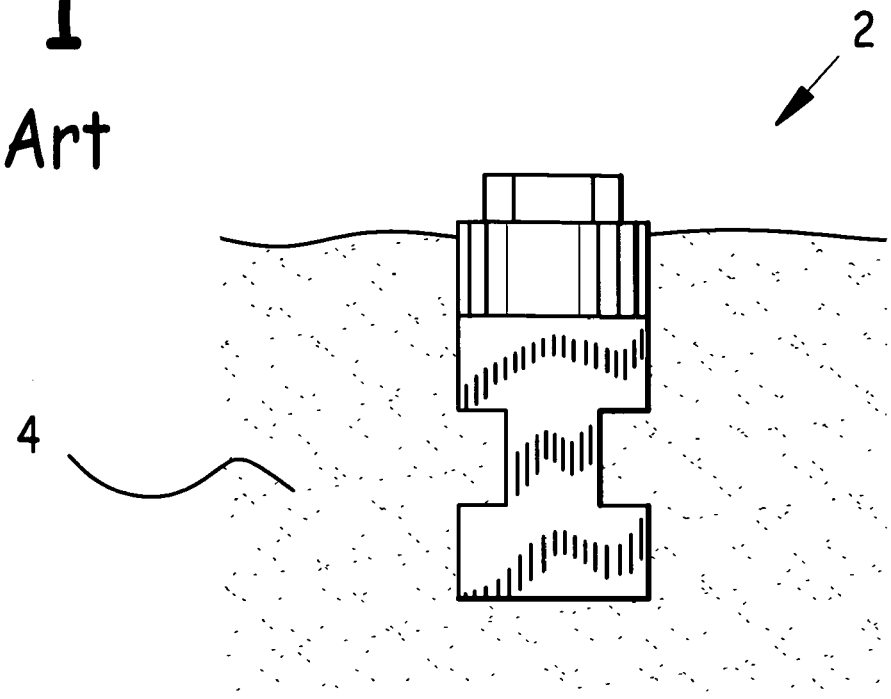
FIG. 1 is a side isometric view of a prior art implant.
Figure 2:
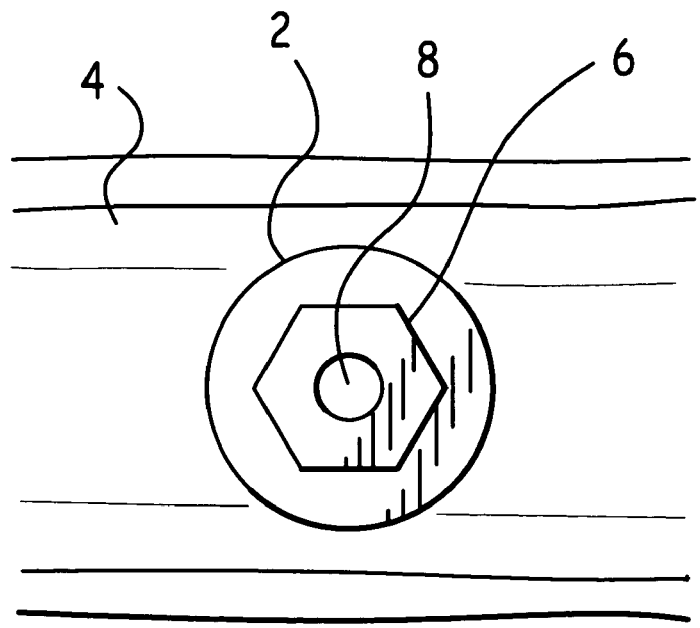
FIG. 2 is a top isometric view of a prior art implant.

FIG. 1 is a side isometric view of a prior art implant 2 installed on bone 4. FIG. 2 is a top isometric view of a prior art implant 2 installed in bone 4. Implant 2 comprises implant indexing means 6 and implant connector 8. A prosthesis or abutment 12 to be installed on implant 2 may have a prosthesis or abutment mating indexing means which mates with implant indexing means 6, so as to prevent rotation of the prosthesis or abutment 12 relative to implant 2. While FIGS. 1 and 2 illustrate implant indexing means 6 to be a male hex shape, and the corresponding mating prosthesis or abutment mating indexing means would then be a female hex shape, many different indexing means shapes are used in the industry, including but not limited to different regular and irregular polygonal cross-sectioned indexing means. In addition, implant indexing means 6 could be a female indexing means and the mating abutment or prosthesis indexing means may be male.

Implant connector 8 is used to attach a prosthesis or abutment 12 to implant 2, by means of a mating connector such as abutment implant connector 14 illustrated in FIGS. 12–15. While the implant connector 8 illustrated in the instant figures is a threaded bore, and the mating prosthesis connector or abutment implant connector 14 would then be a threaded stud, it is intended to fall within the scope of this disclosure that the instant apparatus to remove dental implant 30 comprise any appropriate means to attach to an existing abutment 12 or implant 2. For instance, abutment implant connector 14 could be a threaded bore and implant connector 8 could be a threaded stud, or abutment implant connector 14 and implant connector 8 may be any other appropriate pair of mating connectors.

Figure 3:
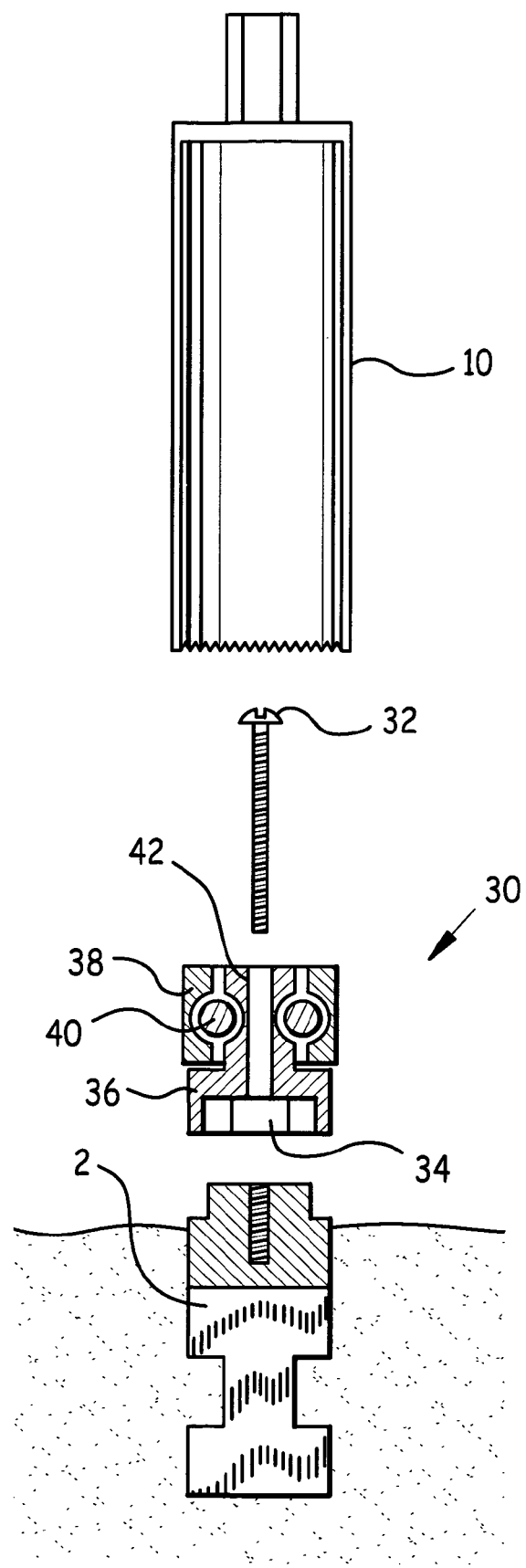
FIG. 3 is a side cross-sectional view of an apparatus to remove dental implant, a trephine burr, and an implant.
Figure 11:
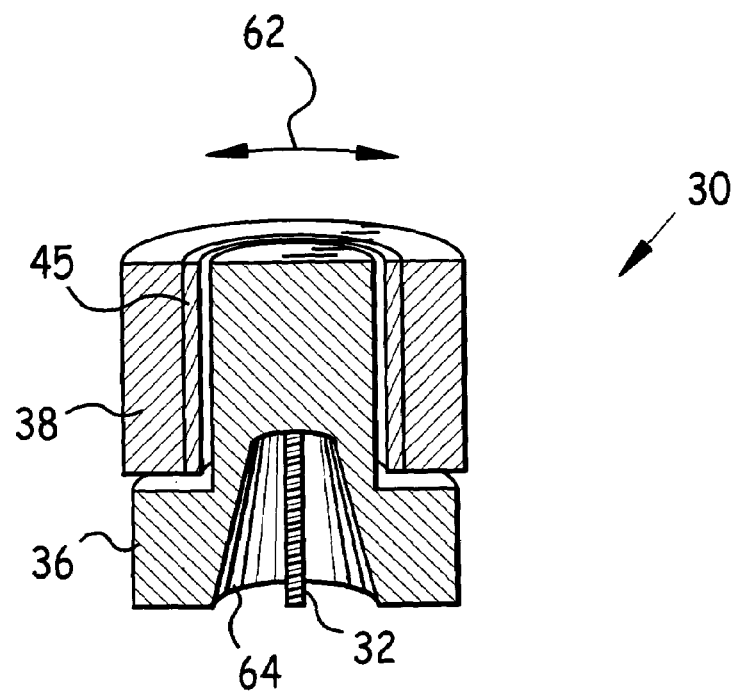
FIG. 11 is a side cross-sectional view of an alternate embodiment apparatus to remove dental implant having a slip ring and a Morse taper.

FIG. 3 is a side cross-sectional view of apparatus to remove dental implant 30, trephine burr 10, and implant 2. Apparatus to remove dental implant 30 is ready to be attached to implant 2 by means of apparatus to remove dental implant fastener 32 through base bore 42. An alternate embodiment apparatus to remove dental implant fastener 32 is depicted in FIG. 11, where apparatus to remove dental implant fastener 32 is a threaded rod rigidly attached to base 36 and sized to mate with a corresponding abutment prosthesis connector 18 (shown in FIG. 13) or implant connector 8, which would be threaded bores. While the instant figures depict two different apparatus to remove dental implant fastener 32 embodiments, it is intended to fall within the scope of this disclosure that the instant apparatus to remove dental implant 30 employ any appropriate apparatus to remove dental implant fastener 32 to attach the instant apparatus to remove dental implant 30 to an implant 2 or abutment 12.

Apparatus to remove dental implant 30 comprises guide ring 38 rotatably attached to base 36. Although FIGS. 3 and 4 illustrate guide ring 38 rotatably attached to base 36 by means of bearings 40, it is intended to fall within the scope of this disclosure that any appropriate means of rotatably attaching guide ring 38 to base 36 be used, including but not limited to slip ring 45 illustrated in FIG. 11, a bushing, low-friction surfaces and/or coatings between guide ring 38 and base 36, etc.

Figure 14:
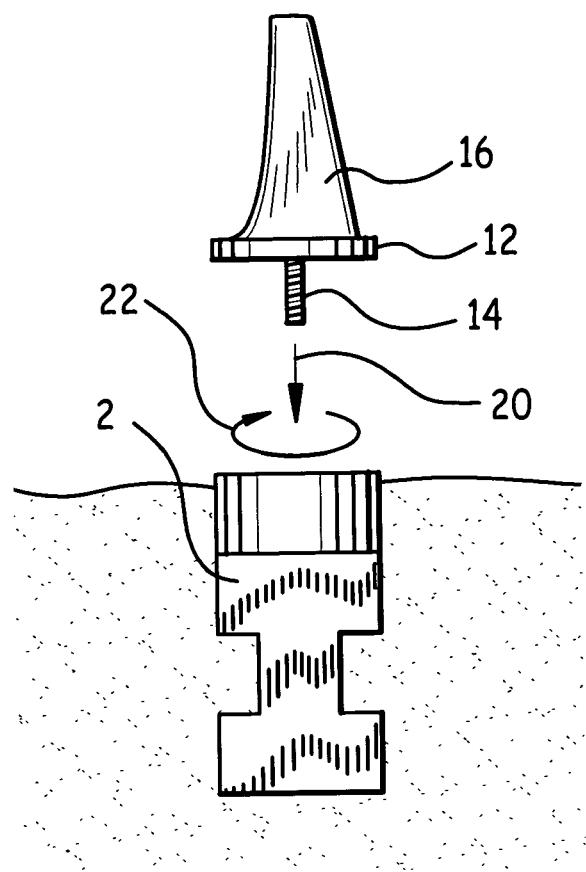
FIG. 14 is a side isometric view of a prior art abutment ready to be installed on an implant.
Figure 15:
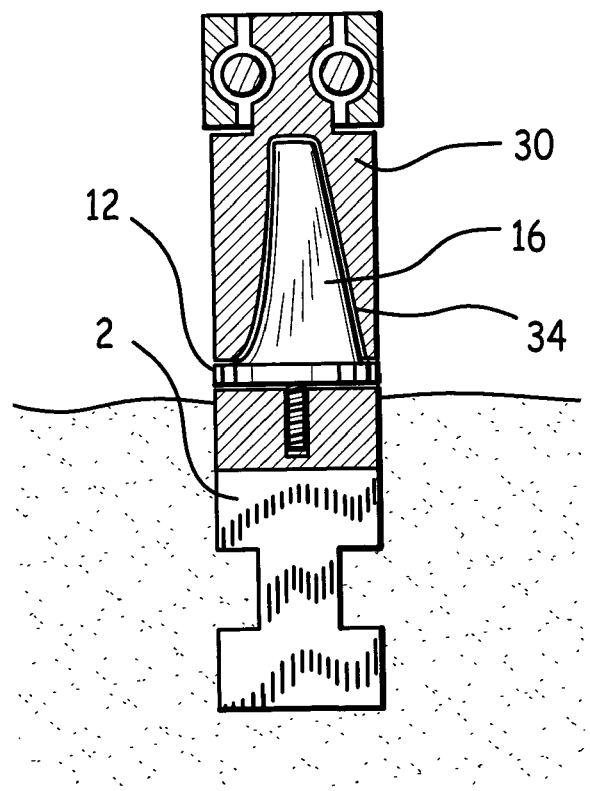
FIG. 15 is a side cross-sectional view of the instant apparatus to remove dental implant installed on an abutment, ready for use.

Apparatus to remove dental implant 30 may further comprise apparatus to remove dental implant indexing means 34 sized to mate with whichever implant indexing means 6 or abutment indexing means 16 is present. Thus, apparatus to remove dental implant indexing means 34 may be male or female, hex shaped, any regular or irregular polygonal cross-sectioned indexing means, irregular or blade or post shaped indexing means such is illustrated in FIGS. 14 and 15, or any other shaped indexing means required to mate with an implant indexing means 6 or abutment indexing means 16.

Figure 4:
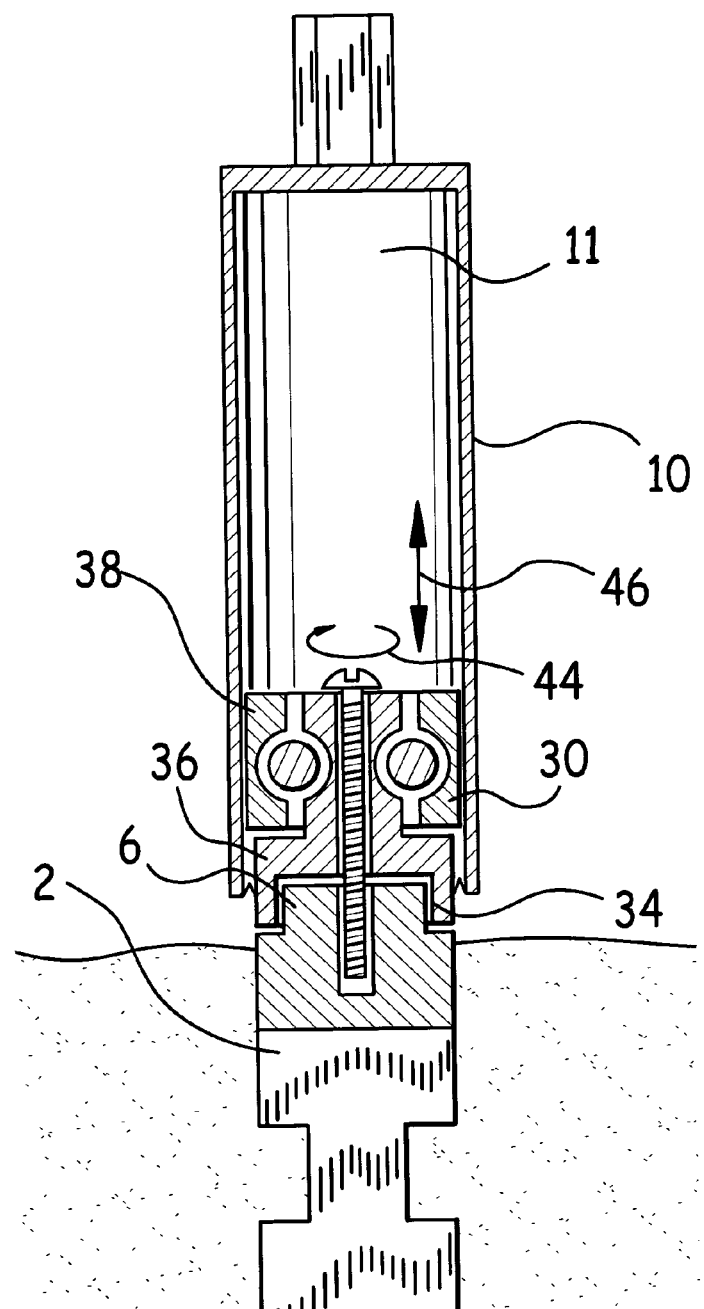
FIG. 4 is a side cross-sectional view of a trephine burr being guided by the instant apparatus to remove dental implant, ready to commence drilling.

FIG. 4 is a side cross-sectional view of apparatus to remove dental implant 30 attached to implant 2 by means of apparatus to remove dental implant fastener 32. Guide ring 38 is free to rotate relative to base 36 as indicated by arrow 44. Because base 36 is attached to implant 2, with apparatus to remove dental implant indexing means 34 (a female hex shape in this case) mated with implant indexing means 6 (a male hex shape in this case), base 36 is held in a constant angular position relative to implant 2, and guide ring 38 is free to rotate relative to both base 36 and implant 2, by virtue of the rotational attachment between guide ring 38 and base 36.

Trephine burr 10 comprises trephine burr bore 11. Guide ring 38 is sized to slidably fit within trephine burr bore 10 as indicated by arrow 46. Thus, when trephine burr 10 is being guided by the instant apparatus to remove dental implant 30, it will be directed downwards around implant 2 and any abutment 12, avoiding cutting into implant 2 and any abutment 12 and avoiding the production of unwanted implant 2 and/or abutment 12 chips.

Figure 5:
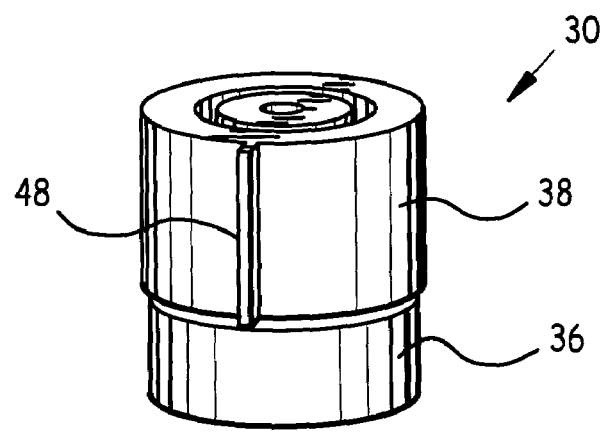
FIG. 5 is a side isometric view of an apparatus to remove dental implant.
Figure 8:
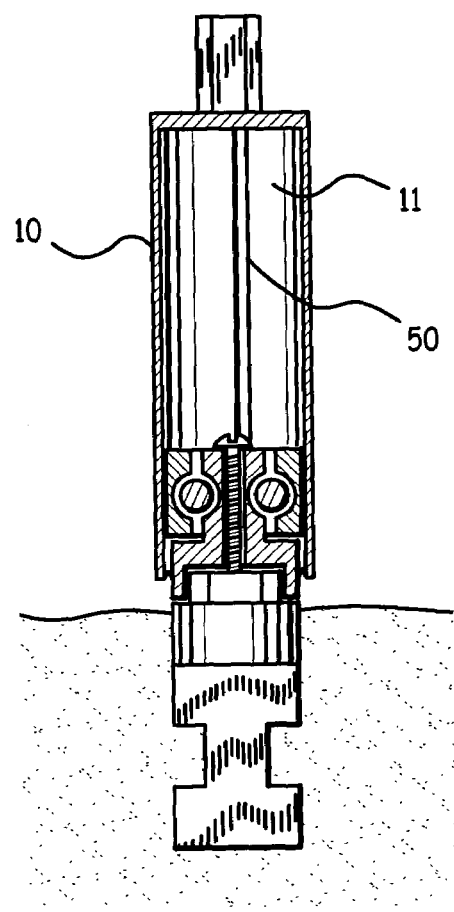
FIG. 8 is a side cross-sectional view of a trephine burr being guided by the instant apparatus to remove dental implant, ready to commence drilling.

FIG. 5 is a side isometric view of an alternate embodiment apparatus to remove dental implant 30 incorporating key 48 disposed on guide ring 38. Key 48 is sized to slidably fit into keyway 50 in trephine burr bore 11 as illustrated in FIG. 8. Keyway 50 is a groove in trephine burr bore 11 parallel to the longitudinal axis of trephine burr 10.

Key 48 in keyway 50 prevents trephine burr 10 from rotating relative to guide ring 38, thus reducing wear on both trephine burr bore 11 and guide ring 38. Although the embodiment illustrated in FIGS. 5 and 8 depict a single key 48 which slidably fits into a single keyway 50, it is intended to fall within the scope of this disclosure that apparatus to remove dental implant 30 may incorporate more than one key 48 on its guide ring 38 (e.g. two, three, four, or more), and that trephine burr bore 11 incorporate a keyway 50 corresponding to each key 48 on guide ring 38, each keyway 50 being located and sized to slidably admit one key 48.

Figure 6:
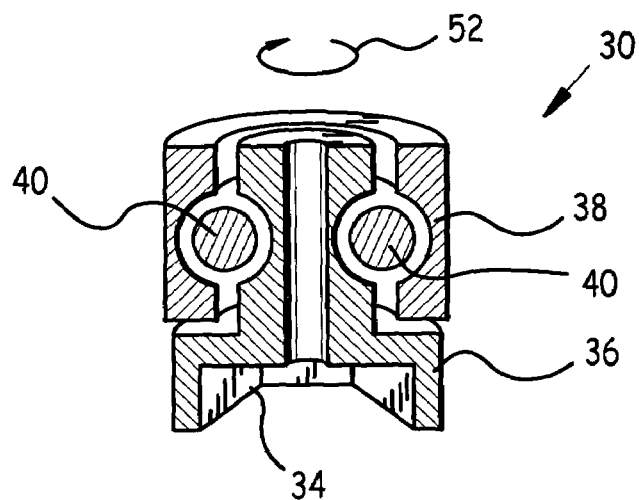
FIG. 6 is a side-cross-sectional view of an apparatus to remove dental implant.

FIG. 6 is a side-cross-sectional view of an apparatus to remove dental implant 30 showing guide ring 38 rotatably attached to base 36 by bearings 40. Guide ring 38 is free to rotate relative to base 36 as indicated by arrow 52. Apparatus to remove dental implant indexing means 34, disposed at an extreme of base 36 opposite guide ring 38, is a female hex shape in this figure.

Figure 7:
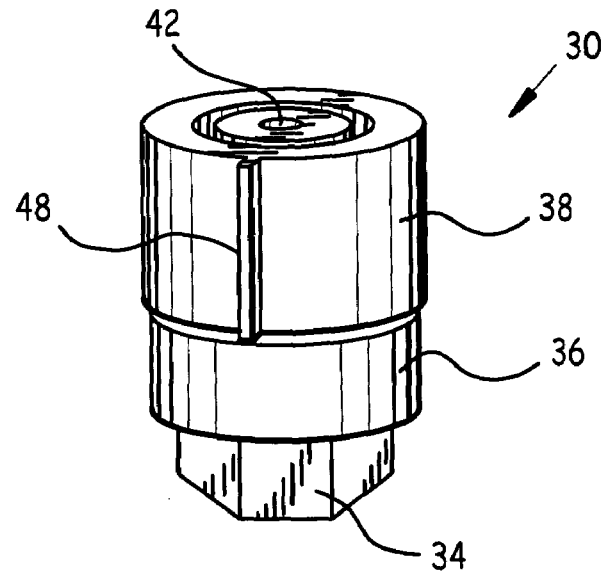
FIG. 7 is a side isometric view of an apparatus to remove dental implant.

FIG. 7 is a side isometric view of an apparatus to remove dental implant 30 including key 48 on guide ring 38. Apparatus to remove dental implant indexing means 34, disposed at an extreme of base 36 opposite guide ring 38, is a male hex shape in this figure.

Figure 9:
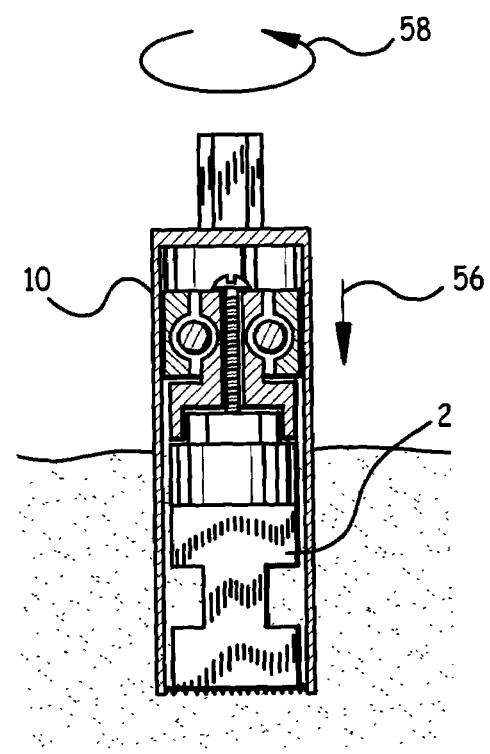
FIG. 9 is a side cross-sectional view of a trephine burr being guided by the instant apparatus to remove dental implant, at the end of the drilling stroke.

FIG. 8 is a side cross-sectional view of trephine burr 10 being guided by the instant apparatus to remove dental implant 30, ready to commence drilling. FIG. 9 is a side cross-sectional view of trephine burr 10 being guided by the instant apparatus to remove dental implant 30, at the end of the drilling stroke.

In use, apparatus to remove dental implant 30 is attached to implant 2 as indicated in FIG. 3 or abutment 12 as indicated in FIGS. 12–15. Then, as depicted in FIG. 8, trephine burr 10 is positioned on apparatus to remove dental implant 30 by slipping trephine burr bore 11 over guide ring 38. If present, each key 48 is aligned with, and inserted into, a corresponding keyway 50.

Next, trephine burr 10 is rotate as indicated by arrow 58 in FIG. 9 (or in the opposite sense, as appropriate) in order to drill around implant 2, as indicated by arrow 56 in FIG. 9, until reaching a depth substantially equal to that of implant 2. Finally, trephine burr 10 is withdrawn and implant 2 is removed in conventional fashion from the hole drilled by trephine burr 10.

Figure 10:
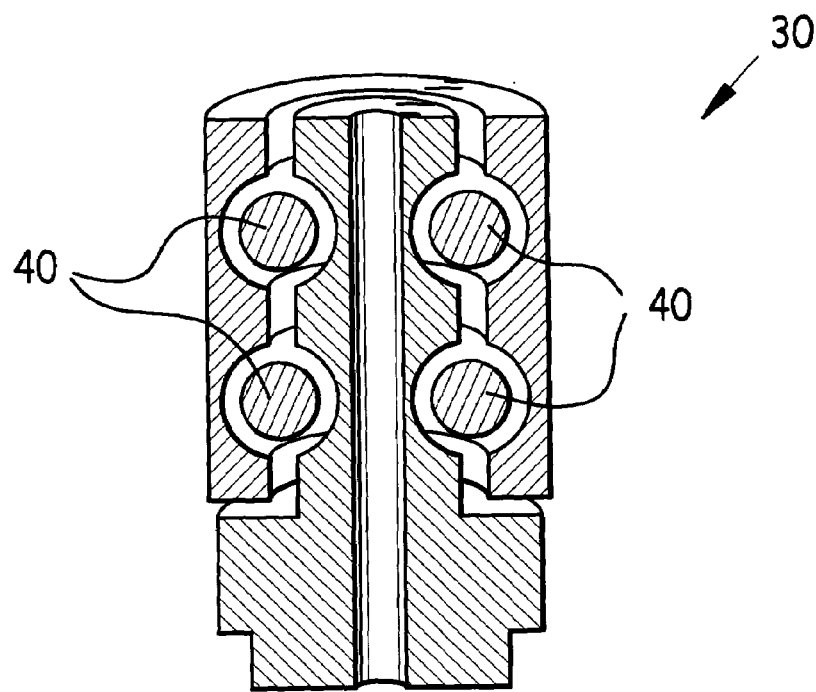
FIG. 10 is a side cross-sectional view of an alternate embodiment apparatus to remove dental implant having two bearings.

FIG. 10 is a side cross-sectional view of an alternate embodiment apparatus to remove dental implant 30 having two sets of bearings 40.

FIG. 11 is a side cross-sectional view of an alternate embodiment apparatus to remove dental implant 30 whose means of rotatably attaching guide ring 38 to base 36 is slip ring 44. Slip ring 45 is made of low-friction material, and functions as a bushing, allowing guide ring 38 to rotate freely relative to base 36 as indicated by arrow 62.

The alternate embodiment apparatus to remove dental implant 30 illustrated in FIG. 11 also depicts base 36 having Morse taper 64 disposed at an extreme of base 36 opposite guide ring 38. It is known within the industry to incorporate a Morse taper on the upper end of implant 2 and/or abutment 12 as a locating device for a prosthesis or abutment to be installed atop the implant 2 or abutment 12. Thus, FIG. 11 depicts an alternate embodiment apparatus to remove dental implant 30 which may be used to guide a trephine burr 10 to remove an implant 2 having a mating Morse taper on its upper end, or an abutment 12 having a mating Morse taper on its upper end.

Figure 12:
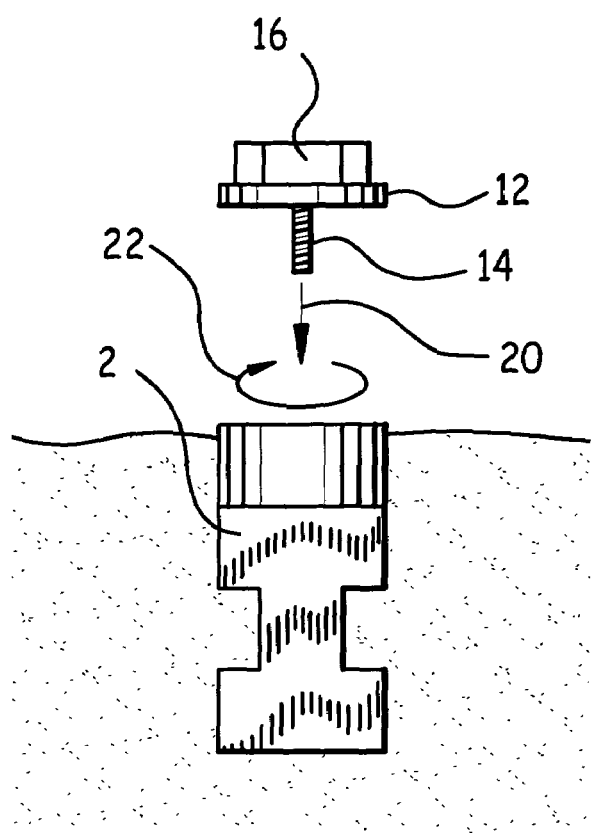
FIG. 12 is a side isometric view of a prior art abutment ready to be installed on an implant.

Abutments 12 are frequently used in the attachment of prostheses to implants 2. This is accomplished by first implanting the implant in bone 4, then attaching abutment 12 to implant 2. Then a prosthesis may be attached to abutment 12. FIGS. 12 and 14 depict installation of different embodiment abutments 12 on implants 12, and FIGS. 13 and 15 depict the instant apparatus to remove dental implant 30 installed and ready to be used to remove the implant 2 with abutment 12 attached.

FIG. 12 is a side isometric view of abutment 12 ready to be installed on implant 2. Abutment 12 may comprise abutment indexing means 16 disposed at one end, and abutment implant connector 14 disposed at an opposite end. Abutment implant connector 14 is sized to mate with implant connector 8. Abutment 12 is attached to implant 2 as indicated by arrows 20 and 22 in FIG. 12. Then apparatus to remove dental implant 30 is attached to abutment 12, using apparatus to remove dental implant fastener 32 and abutment prosthesis fastener 18 as illustrated in FIG. 13.

Figure 13:
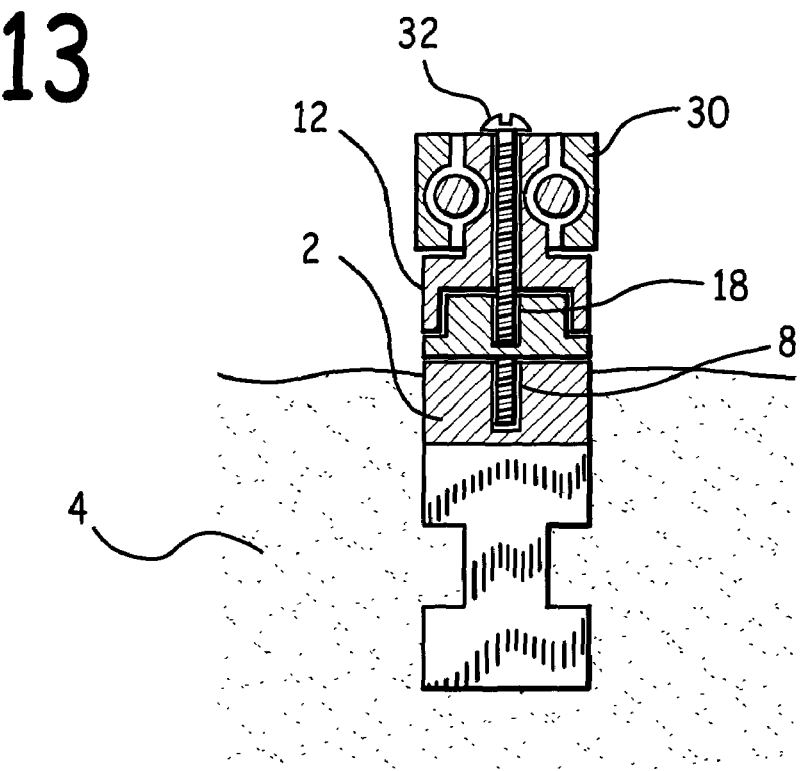
FIG. 13 is a side cross-sectional view of the instant apparatus to remove dental implant installed on an abutment, ready for use.

FIG. 13 is a side cross-sectional view of the instant apparatus to remove dental implant 30 installed on abutment 12, ready for use. In use, a trephine burr 10 is slid over guide ring 38 as described previously, then used to drill into bone 4 to a depth substantially equal to the bottom of implant 2. Trephine burr 10 is then withdrawn, and implant 2 with abutment 12 attached is removed conventionally.

FIG. 14 is a side isometric view of an alternate embodiment abutment 12 ready to be installed on implant 2. Abutment 12 may comprise abutment indexing means 16 disposed at one end, and abutment implant connector 14 disposed at an opposite end. In this case abutment indexing means 16 is a male blade, post, or other irregular shape. Abutment implant connector 14 is sized to mate with implant connector 8. Abutment 12 is attached to implant 2 as indicated by arrows 20 and 22 in FIG. 14. Then apparatus to remove dental implant 30 is attached to abutment 12 as illustrated in FIG. 15.

FIG. 15 is a side cross-sectional view of the instant apparatus to remove dental implant 30 installed on abutment 12, ready for use. In the embodiment apparatus to remove dental implant 30 illustrated in FIG. 15, abutment indexing means 16 is an irregular male blade or post shape, and thus mating apparatus to remove dental implant indexing means 34 is a mating female irregular blade or post shape aperture, as illustrated in FIG. 15. Because abutment indexing means 16 may contain no abutment prosthesis connector 18, apparatus to remove dental implant indexing means 34 is emplaced over abutment indexing means 16, and while apparatus to remove dental implant 30 is being used, it may remain in place due to a frictional fit with abutment indexing means 16, or apparatus to remove dental implant indexing means 34 may be glued to implant indexing means 16.

In use, a trephine burr is slid over guide ring 38 as described previously, then used to drill into bone 4 to a depth substantially equal to the bottom of implant 2. Trephine burr 10 is then withdrawn, and implant 2 with abutment 12 attached is removed conventionally.

Thus, the instant method to remove dental implant comprises the steps of:

A. Providing an apparatus to remove dental implant comprising a guide ring, a base, means of rotatably attaching the guide ring to the base, and means of attaching the base to an implant, said guide ring being sized to slidably fit into a trephine burr bore;

B. Attaching the base to an implant using said means of attaching the base to an implant;

C. Sliding the trephine burr bore over the guide ring;

D. Using the guide ring as a guide, employing the trephine burr to drill into bone in which the implant is implanted, without drilling into the implant.

Where the implant comprises an implant indexing means, the instant method may comprise the further step of providing an apparatus to remove dental implant indexing means in said base sized to mate with the implant indexing means, and mating the implant indexing means with the apparatus to remove dental implant indexing means when attaching the apparatus to remove dental implant to the implant.

Where the guide ring comprises one or more keys, the instant method may comprise the further steps of providing a keyway in the trephine burr bore corresponding to each key, each keyway being located and sized to slidably admit one key, the instant method including the step of slidably inserting each key into a corresponding keyway when sliding the trephine burr bore over the guide ring.

Where an abutment is attached to the implant, the instant method may include the steps of attaching the base to the abutment, and while using the guide ring as a guide, employing the trephine to drill into bone in which the implant is implanted, without drilling into the abutment or the implant.

While a preferred embodiment of the invention has been illustrated herein, it is to be understood that changes and variations may be made by those skilled in the art without departing from the spirit of the appending claims.

DRAWING ITEM INDEX 2 implant
4 bone
6 implant indexing means
8 implant connector
10 trephine burr
11 trephine burr bore
12 abutment
14 abutment implant connector
16 abutment indexing means
18 abutment prosthesis connector
20 arrow
22 arrow
30 apparatus to remove dental implant
32 apparatus to remove dental implant fastener
34 apparatus to remove dental implant indexing means
36 base
38 guide ring
40 bearing
42 base bore
44 arrow
45 slip ring
46 arrow
48 key
50 keyway
52 arrow
56 arrow
58 arrow
60 arrow
62 arrow
64 Morse taper

I claim:

1. An apparatus to remove a dental implant comprising
a guide ring,
a base,
means for rotatably attaching said guide ring to said base, and
means for attaching said base to an implant,
said guide ring being sized to slidably fit into a trephine burr bore.

2. The apparatus to remove a dental implant of claim 1 further comprising apparatus indexing means in said base, said apparatus indexing means being sized to mate with an implant indexing means on said implant.

3. The apparatus to remove a dental implant of claim 2 wherein said means for attaching said base to said implant comprises an apparatus to remove a dental implant fastener through a base bore in said base, said apparatus to remove a dental implant fastener being sized to mate with an implant connector in said implant.

4. The apparatus to remove a dental implant of claim 2 wherein said means for attaching said base to an implant comprises a threaded rod rigidly attached to said base, said threaded rod being sized to mate with an implant connector in said implant.

5. The apparatus to remove a dental implant of claim 2 wherein said apparatus indexing means for is a male protuberance of polygonal cross-section.

6. The apparatus to remove a dental implant of claim 5 wherein said apparatus indexing means is a male hex.

7. The apparatus to remove a dental implant of claim 2 wherein said apparatus indexing means is a female recess of polygonal cross-section.

8. The apparatus to remove a dental implant of claim 7 wherein said apparatus indexing means is a female hex.

9. The apparatus to remove a dental implant of claim 1 further comprising at least one key on said guide ring, each said key being sized to slidably fit into a corresponding keyway in said trephine burr bore.

10. The apparatus to remove a dental implant of claim 9 wherein each said keyway is substantially parallel to a trephine burr longitudinal axis.

11. The apparatus to remove a dental implant of claim 1 wherein said means for rotatably attaching said guide ring to said base comprises ball bearings.

12. The apparatus to a remove dental implant of claim 1 wherein said means for rotatably attaching said guide ring to said base comprises a slip ring or bushing disposed between said guide ring and said base.

13. The apparatus to remove a dental implant of claim 1 wherein said means for rotatably attaching said guide ring to said base comprises a low-friction surface between said guide ring and said base.

14. The apparatus to remove a dental implant of claim 1 further comprising a Morse taper on said base.

15. An apparatus to remove a dental implant comprising
a guide ring,
a base,
means for rotatably attaching said guide ring to said base, and
means for attaching said base to an abutment attached to an implant,
said guide ring being sized to slidably fit into a trephine burr bore.

16. The apparatus to remove a dental implant of claim 15 further comprising apparatus indexing means in said base, said apparatus indexing means being sized to mate with an abutment indexing means on said abutment.

17. The apparatus to remove a dental implant of claim 16 wherein said means for attaching said base to said abutment comprises an apparatus to remove a dental implant fastener through a base bore in said base, said apparatus to remove a dental implant fastener being sized to mate with an abutment prosthesis connector in said implant.

18. The apparatus to remove a dental implant of claim 16 wherein said apparatus indexing means is a male protuberance of polygonal cross-section.

19. The apparatus to remove a dental implant of claim 16 wherein said apparatus indexing means is a female recess of polygonal cross-section.

20. The apparatus to remove a dental implant of claim 16 further comprising at least one key on said guide ring, each said key being sized to slidably fit into a corresponding keyway in said trephine burr bore.

21. A method to remove dental implant comprising the steps of:
  A. Providing an apparatus to remove a dental implant comprising a guide ring, a base, means for rotatably attaching said guide ring to said base, means for attaching said base to an implant, said guide ring being sized to slidably fit into a trephine burr bore;
  B. Attaching said base to an implant using said means for attaching said base to an implant;
  C. Sliding said trephine burr bore over said guide ring; and
  D. Using said guide ring as a guide, employing the trephine burr to drill into bone in which said implant is implanted, without drilling into said implant.

22. The method of claim 21 comprising the further steps of providing apparatus indexing means in said base sized to mate with an implant indexing means, and mating said implant indexing means with said apparatus indexing means when attaching the apparatus to said implant.

23. The method of claim 21 comprising the further steps of providing at least one key on said guide ring and a keyway in said trephine burr bore corresponding to each said key, each said keyway being located and sized to slidably admit one said key, and slidably inserting each said key into a corresponding said keyway when sliding said trephine burr bore over said guide ring.

24. A method to remove dental implant comprising the steps of:
  A. Providing an apparatus to remove a dental implant comprising a guide ring, a base, means for rotatably attaching said guide ring to said base, means for attaching said base to an abutment attached to an implant, said guide ring being sized to slidably fit into a trephine burr bore;
  B. Attaching said base to said abutment using said means for attaching said base to an abutment;
  C. Sliding said trephine burr bore over said guide ring; and
  D. Using said guide ring as a guide, employing the trephine burr to drill into bone in which said implant is implanted, without drilling into said implant or said abutment.

25. The method of claim 24 comprising the further steps of providing apparatus indexing means in said base sized to mate with an abutment indexing means, and mating the abutmemt indexing means with said apparatus indexing means when attaching said apparatus to said abutment.

26. The method of claim 24 comprising the further steps of providing at least one key on said guide ring and a keyway in said trephine burr bore corresponding to each said key, each said keyway being located and sized to slidably admit one key, and slidably inserting each said key into a corresponding said keyway when sliding said trephine burr bore over said guide ring.

* * * * *